United States Patent [19]
Malchesky

[11] Patent Number: 5,932,171
[45] Date of Patent: *Aug. 3, 1999

[54] STERILIZATION APPARATUS UTILIZING CATHOLYTE AND ANOLYTE SOLUTIONS PRODUCED BY ELECTROLYSIS OF WATER

[75] Inventor: Paul S. Malchesky, Painesville Twp., Ohio

[73] Assignee: Steris Corporation, Mentor, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/910,385

[22] Filed: Aug. 13, 1997

[51] Int. Cl.$^6$ .................................................. A61L 2/18
[52] U.S. Cl. .............................. 422/29; 422/14; 422/31; 422/255; 422/292; 422/293; 134/95.2; 134/99.2; 134/100.1; 204/263; 205/351; 205/464
[58] Field of Search ................... 422/28, 29, 31, 422/292, 293, 14, 255; 134/95.1, 95.2, 99.2, 100.1; 204/263; 205/351, 464

[56] References Cited

U.S. PATENT DOCUMENTS

| | | | |
|---|---|---|---|
| 4,470,890 | 9/1984 | Bommaraju et al. | 422/18 |
| 4,710,233 | 12/1987 | Hohmann et al. | 422/22 |
| 4,731,222 | 3/1988 | Kralovic et al. | 422/37 |
| 5,209,909 | 5/1993 | Siegel et al. | 422/292 |
| 5,334,383 | 8/1994 | Morrow | 424/94.4 |
| 5,408,991 | 4/1995 | Iida et al. | 128/4 |
| 5,427,667 | 6/1995 | Bakhir et al. | 204/260 |
| 5,431,877 | 7/1995 | Brucken et al. | 422/12 |

(List continued on next page.)

FOREIGN PATENT DOCUMENTS

| | | |
|---|---|---|
| 706801 | 4/1996 | European Pat. Off. . |
| 4418812 | 12/1995 | Germany . |
| 7327674 | 12/1995 | Japan . |
| 7328100 | 12/1995 | Japan . |
| 7328638 | 12/1995 | Japan . |
| 8038582 | 2/1996 | Japan . |
| 8052475 | 2/1996 | Japan . |
| 8327955 | 12/1996 | Japan . |
| 2294473 | 5/1996 | United Kingdom . |

OTHER PUBLICATIONS

Journal of Hospital Infection, "Antimicrobial Activity of Superoxidized Water", by H. Tanaka, et al., pp. 43–49 (1996).

Sterox the Solution, "Providing Solutions for Your Sterilization Needs", by John Babb (Mar. 1996).

(List continued on next page.)

*Primary Examiner*—Krisanne Thornton
*Assistant Examiner*—Fariborz Moazzam
*Attorney, Agent, or Firm*—Fay, Sharpe, Beall, Fagan, Minnich & McKee, LLP

[57] ABSTRACT

An apparatus (A) for sterilizing medical instruments and other articles includes a tray (12) with an article receiving area (14). An article to be microbially decontaminated is positioned in the receiving area (14) and a microbe blocking lid (10) is closed. A water electrolysis apparatus (30) receives water, splits the water into two separate streams that pass respectively through an anode chamber (34) and a cathode chamber (36), and exposes the streams to an electric field that results in the production of a catholyte solution for cleaning and an anolyte solution for sterilization. The anolyte and catholyte are selectively circulated through the article receiving area (14) by a pump (66) to clean and microbially decontaminate the external surfaces and internal passages of an article located therein. The anolyte or deactivated anolyte provides a sterile rinse solution. A reagent dispensing well (60) receives an ampule (80) or the like. The ampule (80) contains internal compartments which are selectively accessed or opened to dispense detergent concentrate and/or sterilant concentrate reagents into the circulating anolyte and catholyte solutions. A water treatment apparatus (28) dispenses either a salt or a cleaning agent into the water received from the source (24) to vary the electrolysis reaction or to form a cleaning solution to clean and flush the electrolysis apparatus (30), respectively.

11 Claims, 2 Drawing Sheets

U.S. PATENT DOCUMENTS

| | | | |
|---|---|---|---|
| 5,439,654 | 8/1995 | Kochte | 422/292 |
| 5,487,788 | 1/1996 | Kamiya et al. | 134/1 |
| 5,507,932 | 4/1996 | Robinson | 204/228 |
| 5,540,819 | 7/1996 | Bakhir et al. | 205/747 |
| 5,560,816 | 10/1996 | Robinson | 205/687 |
| 5,622,848 | 4/1997 | Morrow | 435/173.1 |
| 5,628,888 | 5/1997 | Bakhir et al. | 204/260 |
| 5,635,040 | 6/1997 | Bakhir et al. | 204/260 |

OTHER PUBLICATIONS

"Electro–Chemical Activation for Water Purification Sterilization Disinfecting", by Monsanto Enviro–Chem Systems, Inc. (1997).

Artificial Organs, "What is Functional Water", by Keiji Kumon vol. 21, No. 1, pp. 2–4, (1997).

Artificial Organs, "Trial of Electrolyzed Strong Acid Aqueous Solution Lavage in the Treatment of Peritonitis and Intraperitoneal Abscess", by Yoshihiro Inoue, et al. vol. 21, No. 1, pp. 28–31, (1997).

Artificial Organs, "Successful Treatment of Mediastinitis after Cardiovascular Surgery Using Electrolyzed Strong Acid Aqueous Solutions", by Hideaki Hayashi, et al. vol. 21, No. 1, pp. 39–42, (1997).

Artificial Organs, "Treatment of Infectious Skin Defects or Ulcers with Electrolyzed Strong Acid Aqueous Solution", by Shuichi Sekiya, et al. vol. 21, No. 1, pp. 32–38, (1997).

Japanese Application, Abstract only (in English), "The evaluation of technique and disinfection the panendoscope after use." (1996) by Nobuto Kinoshita et al.

Japanese Application, Abstract only (in English), "The effect of alkaline and acidic/oxidative functional water on clinical use as washing solution of connecting tubes in hemodialysis cireit." (1996) by Kumeo Ono et al.

Japanese Application, Abstract only (in English), "Effective cleaning and disinfection of endoscopes with acid electrolyzed water." (1996) by Kinuko Sato et al.

Japanese Application, Abstract only (in English), "Cleaning and disinfection of hemo dialyzer reprocessing with acid electrolyzed water." (1996) by Takeshi Shibata et al.

Japanese Application, Abstract only (in English), "Application of soft oxidation potential water to clinical denistry." (1996) by Hiroshi Iwamoto.

STERILIZATION APPARATUS UTILIZING CATHOLYTE AND ANOLYTE SOLUTIONS PRODUCED BY ELECTROLYSIS OF WATER

BACKGROUND OF THE INVENTION

The present invention relates to the sterilization arts. It finds particular application in conjunction with the sterilization of medical instruments and equipment. It will be appreciated, however, that the invention is also applicable to the microbial disinfection or sterilization of other articles such as food processing equipment, pharmaceutical processing equipment, animal cages, and other equipment.

Various methods and apparatus are known for sterilizing medical instruments and devices. For example, medical instruments and other devices are commonly sterilized in a steam autoclave. Autoclaves kill life forms with a combination of high temperature and high pressure. However, steam autoclaves have several drawbacks. The pressure vessels are bulky and heavy. Also, the high temperature and pressure tend to reduce the useful life of medical devices having rubber and plastic components. The medical devices must be pre-cleaned before being placed in the autoclave to remove post-operative bodily tissues and fluids. Moreover, the autoclave sterilization and cool-down cycles take an excessive amount of time, especially in light of the need to minimize the "down time" of expensive, reusable medical devices.

Another known sterilization method utilizes ethylene oxide gas. Ethylene oxide gas sterilization and aeration cycles are even longer than steam autoclave sterilization and cool-down cycles. Ethylene oxide is also hazardous to humans and, therefore, environmental concerns are associated with its use.

Low temperature liquid disinfection and sterilization devices are also known. These devices typically utilize one of several known liquid anti-microbial solutions such as peracetic acid, glutaraldehyde, alcohol, aqueous hydrogen peroxide, and the like. In general, these low temperature liquid systems have been found to be effective. However, hospitals and other health care facilities continue to demand improved sterilization effectiveness and efficiency to reduce the risk of infection and to reduce the percentage of time that expensive medical devices are out of use for sterilization procedures. Also, certain low temperature liquid anti-microbial solutions have fallen out of favor. For example, the use of glutaraldehyde presents environmental concerns and also requires an excessively long cycle time to sterilize, rather than simply disinfect, medical devices. The environmentally harmful glutaraldehyde must be specially disposed of, increasing the cost of sterilization. Alcohol has been found to be destructive to certain plastic components of medical instruments.

Recently, there has been an increased emphasis on the effective cleaning of post-operative debris from the medical instruments and devices. Most known sterilization equipment requires that the contaminated medical devices be precleaned before the sterilization cycle. Others simply sterilize without regard to cleaning which results in a sterile device having sterile debris adhered thereto.

Certain sterilization devices rely upon the filtering of water with a 0.2 $\mu$m or smaller pore size microbe-removal filter media to provide a sterile rinse liquid. However, it would be desirable to provide an additional safeguard against the recontamination of medical devices with rinse liquid by ensuring a virus-free rinse solution. A virus-free rinse solution may not be assured with simple filtration of the rinse liquid. Therefore, there has been found a need to provide a sterilization apparatus that ensures a bacteria and virus free rinse liquid to prevent the accidental recontamination of the sterilized medical device during rinsing operations.

Most recently, the cleaning and decontamination properties of solutions formed via the electrolysis of water under special conditions have been explored. Electrolysis devices are known which receive a supply of tap water, commonly doped with a salt, and perform electrolysis on the water to produce two separate streams of fluid—(i) an anolyte produced at the anode of the electrolysis unit; and, (ii) and catholyte produced at the cathode of the electrolysis unit. The anolyte has been found to be free of all viable microbes, including viruses, and has also been found to have powerful anti-microbial properties, including anti-viral properties. The catholyte has been found to have excellent cleaning properties.

To create these anolyte and catholyte solutions, tap water, often with an added electrically conducting agent such as the salt sodium chloride, is passed through an electrolysis unit or module which has at least one anode chamber and at least one cathode chamber which may be separated from each other by a membrane. An anode contacts the water flowing in the anode chamber, while the cathode contacts the water flowing in the cathode chamber. The anode and cathode are connected across a source of electrical potential to expose the water to an electrical field. The membrane may allow the transfer of electron carrying species between the anode and the cathode but limits fluid transfer between the anode and cathode chambers. The salt and minerals naturally present in and/or added to the tap water undergo oxidation in the anode chamber and reduction in the cathode chamber. The solution resulting at the anode (anolyte) and the solution resulting at the cathode (catholyte) remain separate or are recombined and can be used for a wide variety of different purposes.

The present invention contemplates a new and improved sterilization apparatus for producing and utilizing anolyte and catholyte, as needed, to clean, disinfect or sterilize, and provide a sterile rinse for medical devices.

SUMMARY OF THE INVENTION

In accordance with a first aspect of the present invention, an apparatus for microbially decontaminating a medical device includes an article receiving area for receiving a microbially contaminated medical device. The receiving area has a liquid inlet and a liquid outlet. Water is supplied to an electrolysis apparatus. The electrolysis apparatus includes a water inlet, an anode chamber in fluid communication with the water inlet and having an outlet such that a first flow of water passes therethrough from the water inlet to the anode chamber outlet, and a cathode chamber in fluid communication with the water inlet and having an outlet such that a second flow of water passes therethrough from the water inlet to the cathode chamber outlet. The electrolysis apparatus may also include a membrane separating the anode chamber and the cathode chamber which prevents fluid communication therebetween. However, the membrane does allow the transfer of electron carrying species between the anode and cathode chambers. An anode is positioned in the anode chamber and contacts the first flow of water. A cathode is positioned in the cathode chamber and contacts the second flow of water. A source of electric potential is connected between the anode and cathode to expose the first and second flows to an electric field such that an oxidation reaction occurs in the anode chamber and results in the production of an anolyte solution at the anode chamber outlet and such that a reduction reaction occurs in the cathode chamber and results in the production of a catholyte solution at the cathode chamber outlet. A valve is connected in fluid communication between the outlet of the anode chamber and the liquid inlet to the article receiving area to selectively circulate anolyte to the article receiving area.

In accordance with another aspect of the invention, a method of microbially decontaminating a medical device includes supplying first and second separate streams of water separated by an electron carrying species permeable membrane. An electric field is applied to the first and second streams such that the first stream undergoes an oxidation reaction and such that the second stream undergoes a reduction reaction. A medical device is contacted with liquid from the second stream for a select duration to clean debris from the medical device and is thereafter contacted with liquid from the first stream to microbially decontaminate the medical device.

One advantage of the present invention resides in the production of anolyte and catholyte solutions and the utilization of at least the anolyte solution to kill microbes on a non-sterile article such as a medical device.

Another advantage of the present invention resides in the improved cleaning, sterilizing, and rinsing of medical devices and other articles.

Still another advantage of the present invention is found in the improved control of the properties of the anolyte and catholyte produced by the electrolysis of the water.

Another advantage of the present invention is found in the selective generation of an electrolysis apparatus cleaning solution and the selective flushing of the electrolysis apparatus with the cleaning solution to remove precipitates therefrom.

Another advantage of the present invention is found in the dispensing of a detergent concentrate into a catholyte solution to produce an improved cleaning solution.

A further advantage of the present invention is the utilization of anolyte or deactivated anolyte as a microbe-free rinse solution.

Yet another advantage of the present invention resides in the introduction of a sterilant concentrate into the anolyte to produce a more highly effective anti-microbial solution.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
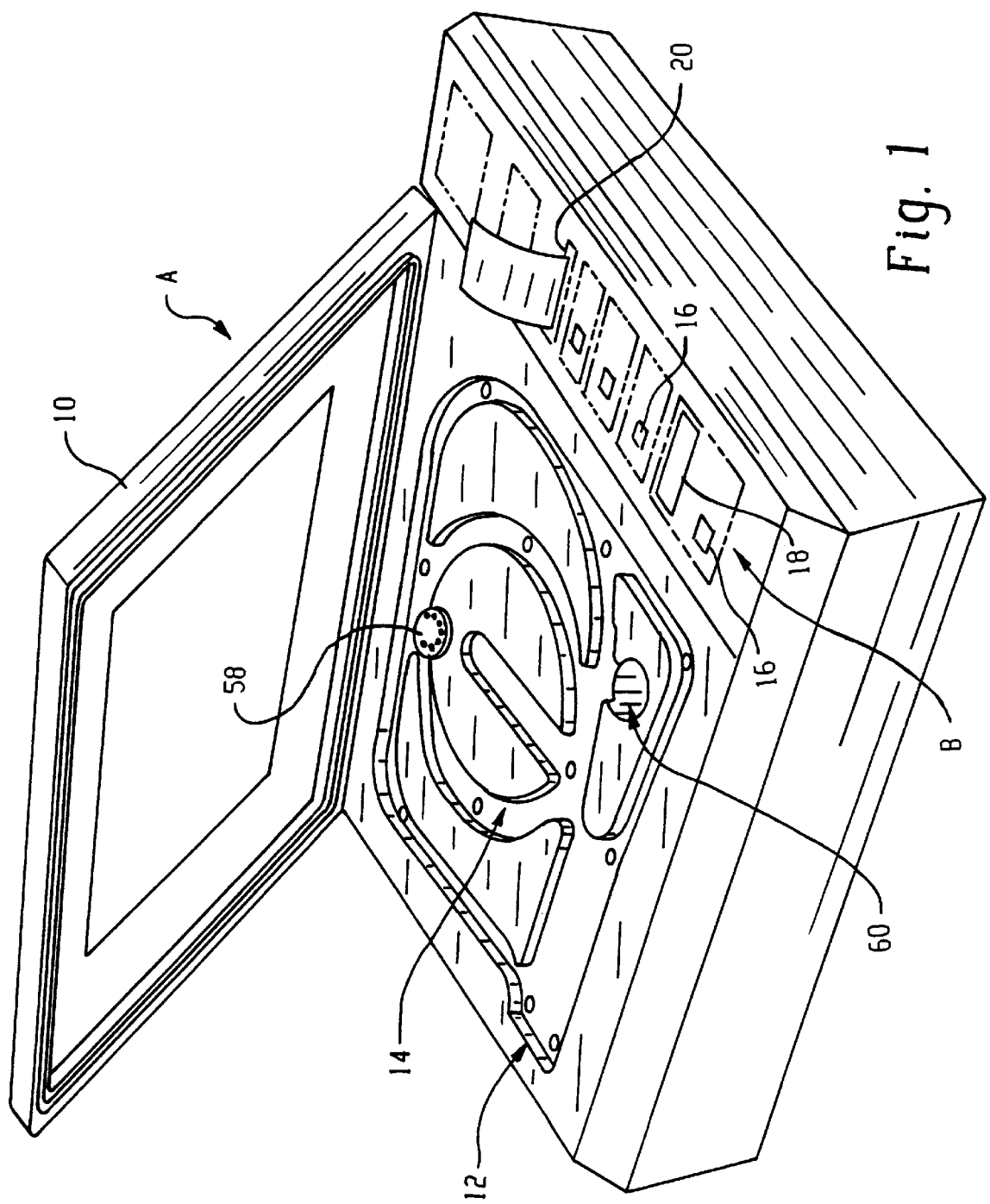
FIG. 1 is a perspective view of a sterilization apparatus in accordance with a first embodiment of the invention; and, FIG. 2 is a diagrammatic illustration of the sterilization apparatus of FIG. 1.

With reference to FIG. 1, a microbial decontamination apparatus A is configured to sit on a counter top or other convenient work surface. A door or lid 10 is openable to provide access to a tray 12 which defines an article receiving region 14 for receiving non-sterile articles that are to be microbially decontaminated, e.g., disinfected or sterilized. In the illustrated embodiment, the tray 12 is configured to receive one or more endoscopes or other elongated, coilable items. Of course, other trays having article receiving regions of different configurations for receiving non-sterile articles or containers holding non-sterile articles are also contemplated. An electronic, microprocessor-based control system B controls the operation of the apparatus A to clean, sterilize, and rinse medical devices. User input devices, such as one or more switches 16 and the like, are provided for user input of sterilization process parameters and other data. Likewise, user output devices such as a visual display 18 and a printer 20 are provided for output of sterilization process parameters to an operator of the apparatus. The control system B controls the operation of the valves, pumps, and other electrical and electromechanical components of the apparatus A as described herein.

Figure 2:
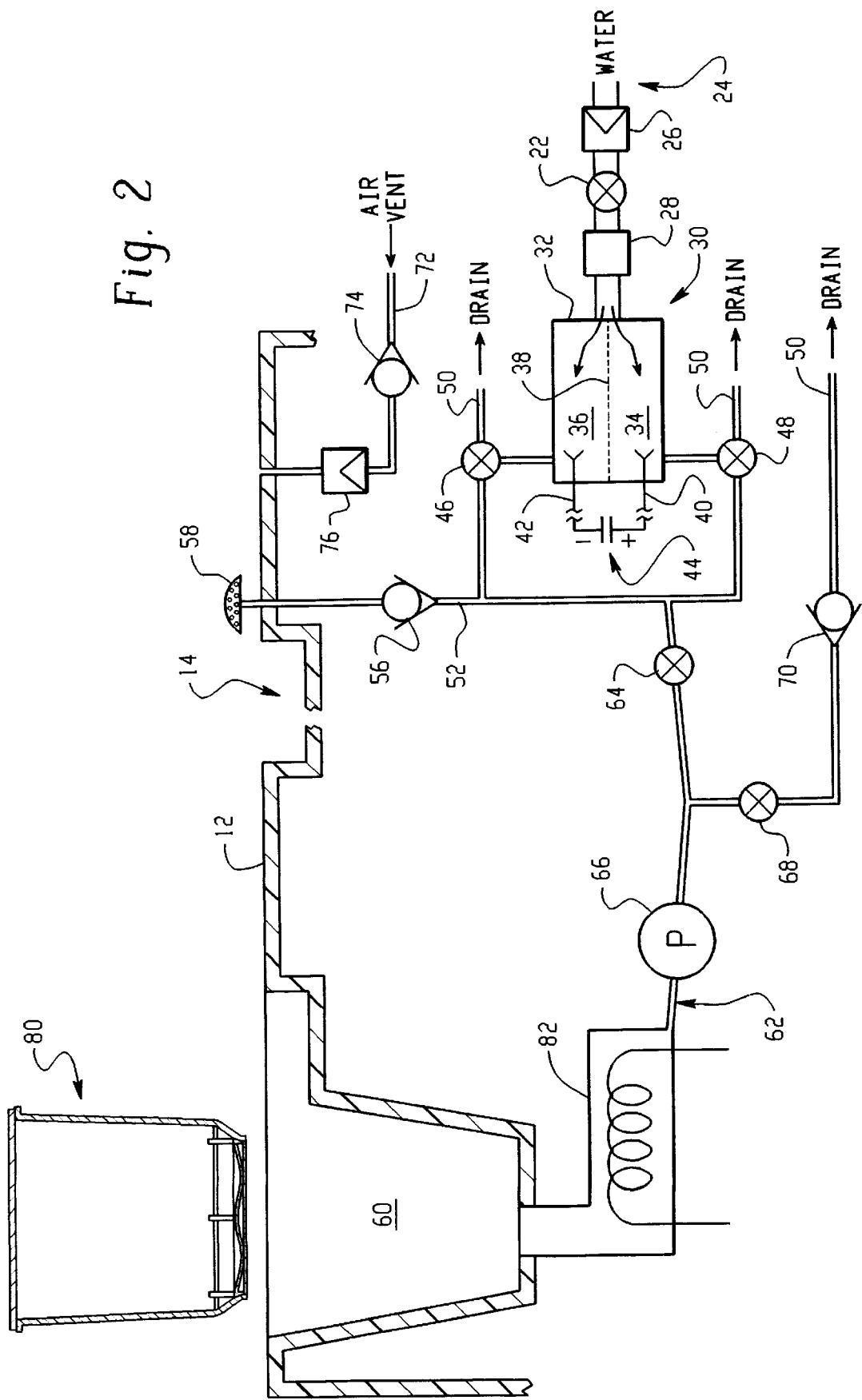

With reference now also to FIG. 2, the apparatus A includes a water supply such as a valve 22 connected to a source of utility or "tap" water 24, to a water reservoir, or the like. A filter 26 filters sand and other particulates from the incoming water. Optionally, the filter 26 is a submicron filter that removes bacteria and other contaminants from the water. A water treatment apparatus 28 adds a selected, metered amount of a salt and/or a buffer to the incoming water based upon the natural salts, minerals, and pH of the water as it is received from the source 24. Sodium chloride has been found to be one suitable salt that may be added by the treatment apparatus 28. Acceptable concentrations of salt in the water, as well as other details of a suitable water electrolysis apparatus are set forth, e.g., in U.S. Pat. Nos. 5,635,040, 5,628,888, 5,427,667, 5,334,383, 5,507,932, 5,560,816, and 5,622,848. The buffer additives to either the incoming water or to the solutions resulting from electrolysis reaction adjust pH and/or add anticorrosives to inhibit corrosion of the medical device or other article being processed.

The incoming water flows under its own pressure or under pressure provided by a pump (not shown) into a water electrolysis apparatus 30 which includes at least one electrolysis unit or module 32 having an anode chamber 34 and a cathode chamber 36 separated by a membrane 38. The membrane 38 divides the incoming water into two flows, a first flow passing through the anode chamber 34 and a second flow passing through the cathode chamber 36. In addition to the water electrolysis units described in the aforementioned U.S. Pat. Nos. 5,635,040, 5,628,888, 5,427,667, 5,334,383, 5,507,932, 5,560,816, and 5,622,848, any other suitable water electrolysis units may be used and the invention is not meant to be limited to any particular electrolysis apparatus.

The anode chamber 34 includes an anode electrode 40 that contacts the first flow of water passing therethrough. The cathode chamber 36 correspondingly includes a cathode electrode 42 that contacts the second flow of water passing therethrough. The membrane 38 prevents the first and second flows from mixing. However, the membrane 38 does allow electron carrying species to transfer between the chambers 34,36. A source of electric potential 44 is connected across the anode 40 and the cathode 42 to expose the flows in the chambers 34,36 to an electric field that produces an oxidation reaction in the anode chamber 34 and a reduction reaction in the cathode chamber 36. These reactions convert the first flow of water into an anolyte solution and convert the second flow of water into a catholyte solution. If desired, first and second reservoirs or holding tanks may be provided in fluid communication with the outlets of the chambers 34,36 to hold the analyte and catholyte solutions, respectively, as they are produced so that these solutions may be used subsequently for cleaning, disinfection, and rinsing operations.

A first valve 46 selectively allows the communication of the catholyte solution from the chamber 36 into a main fill conduit 52 of the apparatus A. A valve 48 is positioned to divert the flow of anolyte from the chamber 34 to a drain 50 or an anolyte storage reservoir and, when so positioned, prevents the flow of anolyte into the fill conduit 52. The diversion of the anolyte ensures a fresh supply of water to the module 32 so that the electrolysis reaction proceeds at the preferred rate. The catholyte is further communicated through a check valve 56 and at least one inlet fixture 58, such as a spray head and/or a liquid distribution manifold, into the article receiving area 14 of the tray 12 and/or into internal lumens or channels formed through a medical device being processed. The catholyte flows by gravity from the article receiving area 14 into a reagent dispensing well 60 and circulation conduits 62 fed from the well 60. Optionally, detergents, wetting agents, corrosion inhibitors, pH buffers, or other additives are added to the catholyte passing through the well. The valves 22 and 46 remain open only until a sufficient amount of catholyte solution is present in the apparatus A for cleaning operations, e.g., until the conduits 62 and well 60 are substantially full. Thereafter, a recirculation valve 64 is opened and a recirculation pump 66 is energized such that the catholyte is drawn by the pump 66 from the reagent dispensing well 60 and pumped to the inlet fixture 58, and any other provided inlet fixtures, such that the catholyte is circulated over the exterior surfaces and through any internal channels of a medical device present in the article receiving area 14 for a selected duration.

After the catholyte is circulated for a selected duration, the recirculation valve 64 is preferably closed and a drain valve 68 is opened such that the pump 66 pumps the catholyte solution to the drain 50 for disposal. A check valve 70 prevents the entrance of fluid from the drain 50 into the apparatus A. As liquid is drained from the apparatus A, air is drawn into the apparatus through a vent 72, a check valve 74, and a microbe-removal filter 76 such as a 0.2 $\mu$m or smaller pore size HEPA filter. During or after the drainage of the catholyte solution, the valve 22, along with at least one of the valves 46,48, is opened to supply anolyte, catholyte, or ordinary water (obtained by deenergizing the anode 40 and cathode 42) to rinse residual debris from the device and the fluid pathways of the apparatus A. The pump 66 is operated and the valve 68 remains open until all catholyte or other rinse liquid is pumped from the apparatus A.

Thereafter, in a manner similar to the supply of the catholyte solution as described above, the valves 22 and 48 are opened to supply anolyte solution to the fill conduit 52, into the article receiving area 14, the reagent dispensing well 60, and the recirculation conduits 62. The valve 46 is opened to divert the catholyte to a drain 50 or a reservoir and to prevent the flow of catholyte to the conduit 52. Once a sufficient amount of anolyte has been supplied, the valves 22,48 are closed and the recirculation valve 64 is again opened. The pump 66 is energized and anolyte is drawn from the well 60 by the recirculation pump and is pumped to the inlet fixture 58 and other inlet fixtures to sterilize the exterior surfaces and internal channels of the medical device positioned in the article receiving area 14. After a selected duration, e.g., 5 to 15 minutes, the valve 64 is closed and the valve 68 is opened such that the anolyte solution is pumped by the pump 66 to the drain 50.

Those skilled in the art will recognize that the catholyte solution and/or anolyte solution may be recirculated through the electrolysis apparatus 30 so that the cleaning properties and disinfection properties thereof, respectively, are maintained at a constant level during cleaning and sterilization operations.

The reagent dispensing well 60 is optionally utilized to dispense reagents from an ampule 80 or other container into the recirculating catholyte and anolyte as needed to enhance the cleaning, or the sterilization and anti-corrosive properties of each, respectively. Alternatively, the apparatus A can utilize a steriliant solution produced solely by mixing ordinary water from the source 24 with a steriliant concentrate, such as peracetic acid, hydrogen peroxide, hypochlorites, or the like. Preferably, pH buffers, wetting agents, and inorganic and organic corrosion inhibitors, such as triazoles and tolytriazoles, are also added. In such case, the catholyte and anolyte solutions may be used only for cleaning and rinsing, respectively. In one embodiment, the ampule 80 contains only sterilant reagents and buffers, such as peracetic acid reagents, and is accessed or otherwise opened during the recirculation of the anolyte to dispense the sterilant reagents, and any provided buffers, into the anolyte to form a sterilant solution. In another embodiment, the ampule 80 includes a first compartment holding detergent concentrate and at least a second compartment holding peracetic acid or other sterilant reagents. The first compartment is accessed during the recirculation of the catholyte to dispense detergent concentrate into the catholyte. The remaining compartments are opened during the recirculation of the anolyte to dispense sterilant reagents into the anolyte. Also, if desired, the well 60 and ampule 80 may be used merely to introduce buffers, anticorrosion agents, and other such reagents into the anolyte solution to inhibit its corrosive properties and to vary its other properties such as pH and the like. A heater 82 is also preferably provided to control the temperature of the recirculating catholyte and anolyte.

To provide an improved sterile rinse solution, the anolyte may be "deactivated" by flowing it through a carbon filter (not shown) or the like. The anolyte may alternatively be deactivated through the application of heat thereto, using the heater 82.

The electrolysis process generates precipitates that can clog the electrolysis module 32. The apparatus A performs regular self-cleaning cycles to remove these deposits. The water inlet valve 22 is opened to allow water to flow into the water treatment apparatus 28 which dispenses a cleaning agent, e.g., citric acid, hydrochloric acid, acetic acid, or another descaling agent, into the water to form a cleaning solution. The cleaning solution is flushed through the electrolysis module 32 and removes the deposits and precipitates therefrom. The anode and cathode are disconnected from the source of electrical potential during this cleaning stage. Preferably, both valves 46 and 48 are set to divert the cleaning solution directly to the drain 50 upon its exit from the chambers 36 and 34, respectively. Alternatively, the cleaning solution may be circulated through all fluid flow paths of the apparatus A.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for cleaning, microbially decontaminating, sterile rinsing, and sterile drying a medical device, the apparatus comprising:

an article receiving area for receiving a microbially contaminated medical device;

a lid closable over the article receiving area in a microbe-blocking relationship;

a liquid inlet to the article receiving area and a liquid outlet from the article receiving area;

a water electrolysis apparatus including:
a water inlet in fluid communication with a water supply,
an anode chamber in fluid communication with the water inlet and having an outlet such that a first flow of water passes therethrough from the water inlet to the anode chamber outlet,
a cathode chamber in fluid communication with the water inlet and having an outlet such that a second flow of water passes therethrough from the water inlet to the cathode chamber outlet,
a membrane separating the anode chamber and the cathode chamber and preventing fluid communication between the anode and cathode chamber, said membrane allowing electron carrying species transfer between the anode and cathode chambers,
an anode positioned in the anode chamber to contact the first flow of water and a cathode positioned in the cathode chamber to contact the second flow of water, and,
a source of electric potential connected between the anode and cathode to expose the first and second flows to an electric field such that an oxidation reaction occurs in the anode chamber resulting in the production of an anolyte solution at the anode chamber outlet, and such that a reduction reaction occurs in the cathode chamber resulting in the production of a catholyte solution at the cathode chamber outlet;

a valve assembly connected in fluid communication between the outlet of the anode chamber and the liquid inlet to the article receiving area and between the outlet of the cathode chamber and the liquid inlet to the article receiving area to selectively and separately circulate each of anolyte and catholyte to the article receiving area for contacting the medical device;

a recirculation pump connected in fluid communication between the liquid outlet of the article receiving area and the liquid inlet to the article receiving area to recirculate one of the anolyte and catholyte through the article receiving area for a select duration;

a reagent dispensing system fluidically connected between the article receiving area and the recirculation pump for dispensing a pH buffer into at least one of the recirculating catholyte and anolyte to substantially neutralize the pH of the at least one of the recirculating anolyte and catholyte;

a submicron water filter in fluid communication with the water supply for filtering microbes from water flowing into said apparatus to provide a sterile rinse liquid to said article receiving area for rinsing residual anolyte from said medical device in said article receiving area;

an air inlet to the article receiving area; and, a submicron air filter connected between the air inlet and the article receiving area for removing airborne microbes from the air entering the article receiving area to provide sterile drying air for contacting the medical device.

2. The apparatus as set forth in claim 1, wherein said reagent dispensing system comprises:
a well for receiving an ampule containing said pH buffer, said well including means for selectively opening the ampule to dispense the contents of the ampule into the at least one of the anolyte and catholyte passing through the well to inhibit corrosion of said medical device.

3. The apparatus as recited in claim 1 further including:
a heater in fluid communication with the pump for heating the one of the anolyte and catholyte recirculated through the article receiving area.

4. The apparatus as set forth in claim 1 further including:
a water treatment apparatus positioned in fluid communication between the electrolysis apparatus and the water supply means for dispensing at least a salt into the received water before the water enters the electrolysis apparatus.

5. An apparatus for cleaning, microbially decontaminating, and drying a medical device, said apparatus comprising:

an article receiving area for receiving a microbially contaminated medical device;

a lid closable over the article receiving area in a microbe blocking relationship;

a liquid inlet to the article receiving area and a liquid outlet from the article receiving area;

a water electrolysis apparatus including:
a water inlet in fluid communication with a water supply,
an anode chamber in fluid communication with the water inlet and having an outlet such that a first flow of water passes therethrough from the water inlet to the anode chamber outlet,
a cathode chamber in fluid communication with the water inlet and having an outlet such that a second flow of water passes therethrough from the water inlet to the cathode chamber outlet,
a membrane separating the anode chamber and the cathode chamber and preventing fluid communication between the anode and cathode chamber, said membrane allowing electron carrying species transfer between the anode and cathode chambers,
an anode positioned in the anode chamber to contact the first flow of water and a cathode positioned in the cathode chamber to contact the second flow of water, and,
a source of electric potential connected between the anode and cathode to expose the first and second flows to an electric field such that an oxidation reaction occurs in the anode chamber resulting in the production of an anolyte solution at the anode chamber outlet, and such that a reduction reaction occurs in the cathode chamber resulting in the production of a catholyte solution at the cathode chamber outlet;

a valve assembly connected in fluid communication between the outlet of the anode chamber and the liquid inlet to the article receiving area and between the outlet of the cathode chamber and the liquid inlet to the article receiving area to selectively and separately circulate each of anolyte and catholyte to the article receiving area for contacting the medical device;

a recirculation pump connected in fluid communication between the liquid outlet of the article receiving area and the liquid inlet to the article receiving area to recirculate one of the anolyte and catholyte through the article receiving area for a select duration;

a reagent dispensing system fluidically connected between the article receiving area and the recirculation pump for dispensing a pH buffer into at least one of the recirculating catholyte and anolyte;

a submicron water filter in fluid communication with the water supply for filtering bacteria from water flowing into said apparatus to provide a sterile rinse liquid to said article receiving area for rinsing residual anolyte from said medical device in said article receiving area; and, a water treatment apparatus positioned in fluid communication between the electrolysis apparatus and the water supply means for selectively dispensing at least a descaling agent into the received water before the water enters the electrolysis apparatus to form a cleaning solution for removing deposits and precipitates from said electrolysis apparatus as needed.

6. A method of cleaning and microbially decontaminating a medical device, said method comprising:

placing a microbially contaminated medical device in a device receiving area;

closing a lid over the device receiving area to enclose the device receiving area in a microbe-blocking condition;

supplying first and second separate streams of water separated by an electrically conducting agent permeable membrane in a water electrolysis cell;

applying an electric field across the first and second streams such that the first stream undergoes an oxidation reaction and such that the second stream undergoes a reduction reaction;

while diverting liquid of the first stream away from the device receiving area, flowing the liquid of the second stream to the device receiving area and over the exterior surfaces and through internal channels of the device in the device receiving area for a select duration to remove biological debris from the device;

draining the liquid from the second stream from the device receiving area;

while diverting liquid from the second stream away from the device receiving area, flowing liquid of the first stream to the device receiving area and over exterior surfaces and through internal channels of the device in the device receiving area for a select duration to microbially decontaminate the exterior surfaces and internal channels of the device;

draining the liquid of the first stream from the device receiving area;

receiving rinse water from a source;

passing the rinse water through a microbe-removal filter to remove microbes from the rinse water and provide a sterile rinse liquid;

flowing the sterile rinse liquid over the exterior surfaces and through internal channels of the device in the article receiving area to rinse residual liquid from the first stream from the device;

training the sterile rinse liquid from the device receiving area; and, receiving air into the device receiving area through a microbe-removal filter so that sterile drying air flows over the exterior surfaces and through internal channels of the device in the device receiving area and dries the device.

7. The method as recited in claim 6 further comprising:

dispensing a select amount of a descaling agent into the water forming the first and second streams prior to applying the electric field to the first and second streams to form a precipitate cleaning solution; end, flowing the cleaning solution through the water electrolysis cell to remove precipitates from the cell prior to application of the electric field to the first and second streams.

8. The method as set forth in claim 6 further comprising:

dispensing a sterilant concentrate into the first stream and flowing the liquid of the first stream over the exterior surfaces and through internal channels of the device in the device receiving area.

9. The method as set forth in claim 6 further including, after the step of flowing the first stream:

deactivating the liquid from the first stream by at least one of passing the liquid through a deactivating filter and heating the liquid of the first stream; and, rinsing the exterior and internal channels of the device with the deactivated liquid of the first stream.

10. A method of microbially decontaminating a medical device, said method comprising:

a) supplying first and second separate streams of water separated by an electrically conducting agent permeable membrane;

b) applying an electric field to the first and second streams such that the first stream undergoes an oxidation reaction to form an acidic anolyte solution and such that the second stream undergoes a reduction reaction to form an alkaline catholyte solution;

c) circulating liquid from the second stream over the medical device for a select duration to clean biological debris from the medical device;

d) dispensing a pH buffer into the liquid of the first stream to substantially neutralize the liquid from the first stream so that corrosion of the medical device, itself, is inhibited and, thereafter, circulating liquid from the first stream over the medical device for a select duration to microbially decontaminate the medical device.

11. The method as set forth in claim 10 further comprising:

passing tap water through a submicron filter to remove microbes from the tap water to provide a microbe-free rinse solution; and after contacting the device with the liquid of the first stream to microbially decontaminate the device, contacting the device with the microbe-free rinse solution for a select duration to remove residue from the device.

* * * * *